United States Patent
Hsieh (10) Patent No.: US 10,512,637 B2
(45) Date of Patent: Dec. 24, 2019

(54) USE OF INHIBITOR OF CYSTINE-GLUTAMATE TRANSPORTER

(71) Applicant: CHINA MEDICAL UNIVERSITY, Taichung (TW)

(72) Inventor: Chia-Hung Hsieh, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 0 days.

(21) Appl. No.: 15/579,461

(22) PCT Filed: Jun. 6, 2016

(86) PCT No.: PCT/CN2016/085002
§ 371 (c)(1),
(2) Date: Dec. 4, 2017

(87) PCT Pub. No.: WO2016/192687
PCT Pub. Date: Dec. 8, 2016

(65) Prior Publication Data
US 2018/0153865 A1 Jun. 7, 2018

Related U.S. Application Data

(60) Provisional application No. 62/171,315, filed on Jun. 5, 2015.

(51) Int. Cl.
| | |
|---|---|
| C07D 213/30 | (2006.01) |
| A61K 31/4402 | (2006.01) |
| A61K 31/44 | (2006.01) |
| A61K 31/655 | (2006.01) |
| A61P 25/36 | (2006.01) |
| A61P 25/32 | (2006.01) |
| A61K 45/06 | (2006.01) |

(52) U.S. Cl.
CPC .......... *A61K 31/4402* (2013.01); *A61K 31/44* (2013.01); *A61K 31/655* (2013.01); *A61K 45/06* (2013.01); *A61P 25/32* (2018.01); *A61P 25/36* (2018.01)

(58) Field of Classification Search
CPC .......................... C07D 213/30; A61K 31/4402
See application file for complete search history.

(56) References Cited

U.S. PATENT DOCUMENTS

| | | | | |
|---|---|---|---|---|
| 7,829,709 B1* | 11/2010 | Cook | .................... | C07D 241/08 544/336 |
| 2014/0155440 A1* | 6/2014 | Cook | .................... | C07K 5/1008 514/364 |

FOREIGN PATENT DOCUMENTS

| | | | |
|---|---|---|---|
| WO | WO 2007084541 A2 | 7/2007 | |
| WO | 2008042795 A2 | 4/2008 | |
| WO | WO 2014197536 A2 | 12/2014 | |
| WO | WO 2015070034 A1 | 5/2015 | |

OTHER PUBLICATIONS

Kau et al., Neuroscience, 2008, 155(2):530-7 (see Abstract).*
Bridges et al. British Journal of Pharmacology, 2012, 165:20-34.*
Albrecht, P., et al., Mechanisms of oxidative glutamate toxicity: the glutamate/cystine antiporter system xc—as a neuroprotective drug target. CNS Neural Disord Drug Targets, 2010. 9(3): p. 373-82.
Baker, D.A., et al., Neuroadaptations in cystine-glutamate exchange underlie cocaine relapse. Nat Neurosci, 2003. 6(7): p. 743-9.
Bridges, R.J, NR. Natale, and S.A. Patel, System xc(-) cystine/glutamate antiporter: an update on molecular pharmacology and roles w ithin the CNS. Br J Pharmacol, 2012. 165(1): p. 20-34.
Buckingham, S.C., et al., Glutamate release by primary brain tumors induces epileptic activity. Nat Med, 2011. 17(10): p. 1269-74.
Chung, WJ, et al., Inhibition of cystine uptake disrupts the growth of primary brain tumors. J Neurosci, 2005. 25(31): p. 7101-10.
De Bundel, D., et al., Loss of system x(c)—does not induce oxidative stress but decreases extracellular glutamate in hippocampus and influences spatial working memory and limbic seizure susceptibility. J Neurosci, 2011. 31(15): p. 5792-803.
Del Arco, A., et al., Amphetamine increases the extracellular concentration of glutamate in striatum of the awake rat: involvement of high affinity transporter mechanisms. Neuropharmacology, 1999. 38(7): p. 943-54.
Ding, Z.M, et al., Alcohol drinking and deprivation alter basal extracellular glutamate concentrations and clearance in the mesolimbic system of alcohol-preferring (P) rats. Addict Biol, 2013. 18(2): p. 297-306.
Gonzales, R.A. and JN Jaworski, Alcohol and glutamate. Alcohol Health Res World, 1997. 21(2): p. 120-7.
Knackstedt, L.A., et al., The role of cystine-glutamate exchange in nicotine dependence in rats and humans. Biol Psychiatry, 2009. 65(10): p. 841-5.
Lewerenz, J, et al., The cystine/glutamate antiporter system x(c)(-) in health and disease: from molecular mechanisms to novel therapeutic opportunities. Antioxid Redox Signal, 2013. 18(5): p. 522-55.
Moghaddam, B., et al., Activation of glutamatergic neurotransmission by ketamine: a novel step in the pathway from NMDA receptor blockade to dopaminergic and cognitive disruptions associated with the prefrontal cortex. J Neurosci, 1997. 17(8): p. 2921-7.
Peana, A.T, G. Muggironi, and F. Bennardini, Change of cystine/glutamate antiporter expression in ethanol-dependent rats. Front Neurosci, 2014. 8: p. 311.
Peters, J and TJ De Vries, Glutamate mechanisms underlying opiate memories. Cold Spring Harb Perspect Med, 2012. 2(9): p. a012088.
Saellstroem Baum, S., et al., Nicotine stimulation on extracellular glutamate levels in the nucleus accumbens of ethanol-withdrawn rats in vivo. Alcohol Clin Exp Res, 2006. 30(8): p. 1414-21.
Sato, H., et al., Cloning and expression of a plasma membrane cystine/glutamate exchange transporter composed of two distinct proteins. J Biol Chem, 1999. 274(17): p. 11455-8.

(Continued)

*Primary Examiner* — Rei Tsang Shiao
(74) *Attorney, Agent, or Firm* — Duane Morris LLP (57) ABSTRACT

The invention surprisingly found that agents that inhibit system $x_c^-$ provide the therapeutic intervention in substance-related and addictive disorders and the treatment and/or prevention in substance-mediated brain damage and confirms that system $x_c^-$ is a promising therapeutic target for substance-induced addiction and brain damage.

16 Claims, 6 Drawing Sheets

(56) References Cited

OTHER PUBLICATIONS

Shyu, WC., et al., Secretoneurin promotes neuroprotection and neuronal plasticity via the Jak2/Stat3 pathway in murine models of stroke. J Clin Invest, 2008. 118(1): p. 133-48.
Tzschentke, TM and WJ Schmidt, Glutamatergic mechanisms in addiction. Mal Psychiatry, 2003. 8(4): p. 373-82.
Williams, JM et al., Cocaine increases medial prefrontal cortical glutamate overflow in cocaine-sensitized rats: a time course study. Eur J Neurosci, 2004. 20(6): p. 1639-46.
Supplementary European Search Report in EP Application No. 16802610.2, dated Jan. 4, 2019, in 12 pages.
Anonymous: Effects of Sulfasalazine on BOLD Response to Alcohol Cues, ClinicalTrials.gov•Sep. 22, 2014 (Sep. 22, 2014), 8 pages. Retrieved from the Internet: URL:https://clinicaltrials.gov/ct2/show/re cord/NCT01312129 [retrieved on Dec. 7, 2018].
Patel et al: "Emerging roles of system antiporter and its inhibition in CNS disorders", Molecular Membrane Biology., vol. 32, No. 4, Oct. 27, 2015 (Oct. 27, 2015), pp. 89-116.
European Office Action in EP Application No. 16802610.2, dated Oct. 24, 2019, in 10 pages.
anonymous: "Effects of Sulfasalazine on BOLD Response to Alcohol Cues—study results", ClinicalTrials.gov, Sep. 22, 2014 (Sep. 22, 2014), Retrieved from the Internet: URL:https://www.clinicaltrials.gov.ct2/show/results/NCT01312129 [retrieved on Jul. 9, 2019]; 7 pages.
Statistical Analysis of the results presented in "Effects of Sulfasalazine on BOLD Response to Alcohol Cues" anonymous: "Effects of Sulfasalazine on BOLD Response to Alcohol Cues—study results", ClinicalTrials.gov, Sep. 22, 2014 (Sep. 22, 2014), Retrieved from the Internet: URL:https://www.clinicaltrials.gov.ct2/show/results/NCT01312129 [retrieved on Jul. 9, 2019]; 2 pages.
Evans, Suzette M et al: "A pilot double-blind treatment trial of memantine for alcohol dependence", Alcoholism Clinical and Experimental Research, vol. 31, No. 5, May 2007 (May 2007), pp. 775-782, ISSN: 0145-6008.
Muir, Alexander et al: "Environmental cystine drives glutamine anaplerosis and sensitizes cancer cells to glutaminase inhibition", eLIFE, vol. 6, Aug. 15, 2017 (Aug. 15, 2017), ISSN: 2050-084X, 27 pages.
Tomi, Masatoshi et al: "Induction of xCT gene expression and L-cystine transport activity by diethyl maleate at he inner blood-retinal barrier", IOVS, vol. 43, No. 3, Mar. 2002 (Mar. 2002), pp. 774-779.

* cited by examiner

USE OF INHIBITOR OF CYSTINE-GLUTAMATE TRANSPORTER

RELATED APPLICATIONS

This application is a 371 National Stage Application of International Application No. PCT/CN2016/085002, filed on Jun. 6, 2016, which claims the benefit of U.S. Provisional Patent Application No. 62/171,315, filed on Jun. 5, 2015, which is incorporated herein by reference.

FIELD OF THE INVENTION

The present invention is related to a new use of inhibitor of cystine-glutamate transporter, and in particular, is related to a method for improving treatments for a substance-related and addictive disorder or a brain damage induced by substance-related and addictive disorder.

BACKGROUND OF THE INVENTION

Substance-use disorders produce addiction and brain damage for which there is no reliable successful therapy, mainly due to lack of understanding of its pathobiology. Dependence upon drugs of addiction causes major health problems worldwide. For example, alcohol abuse and alcohol dependence can cause liver, pancreatic and kidney disease, heart disease, increased incidence of many types of cancer, insomnia, depression, anxiety, and even suicide. Nicotine addiction is linked to disease states such as leukemia, cataracts, and pneumonia; it is the cause of about one-third of all cancer deaths, the foremost of which is lung cancer. Another major health problem is caused by cocaine abuse. Physical effects of cocaine use include constricted blood vessels, dilated pupils, and increased temperature, heart rate, and blood pressure. It has been shown that many aspects of drug abuse and dependence involve changes in glutamate neurotransmission.

It has been realized that glutamate plays a central role in processes underlying the development and maintenance of addiction (Tzschentke, T. M. and W. J. Schmidt, *Glutamatergic mechanisms in addiction. Mol Psychiatry,* 2003. 8(4): p. 373-82). These processes include reinforcement, sensitization, habit learning and reinforcement learning, context conditioning, craving and relapse. It has been known that many substances, such as alcohol, cocaine, nicotine, ketamine, amphetamine and opiate, are able to promote the elevation of extracellular glutamate levels (Ding, Z. M., et al., *Alcohol drinking and deprivation alter basal extracellular glutamate concentrations and clearance in the mesolimbic system of alcohol-preferring (P) rats. Addict Biol,* 2013. 18(2): p. 297-306; Williams, J. M. and J. D. Steketee, *Cocaine increases medial prefrontal cortical glutamate overflow in cocaine-sensitized rats: a time course study. Eur J Neurosci,* 2004. 20(6): p. 1639-46; Saellstroem Baum, S., et al., *Nicotine stimulation on extracellular glutamate levels in the nucleus accumbens of ethanol-withdrawn rats in vivo. Alcohol Clin Exp Res,* 2006. 30(8): p. 1414-21; Moghaddam, B., et al., *Activation of glutamatergic neurotransmission by ketamine: a novel step in the pathway from NMDA receptor blockade to dopaminergic and cognitive disruptions associated with the prefrontal cortex. J Neurosci,* 1997. 17(8): p. 2921-7; Del Arco, A., et al., *Amphetamine increases the extracellular concentration of glutamate in striatum of the awake rat: involvement of high affinity transporter mechanisms. Neuropharmacology,* 1999. 38(7): p. 943-54; and Peters, J. and T. J. De Vries, *Glutamate mechanisms underlying opiate memories. Cold Spring Harb Perspect Med,* 2012. 2(9): p. a012088). However, the mechanism of substance-increased extracellular glutamate levels is poorly understood.

Although alcohol has been determined to be the inhibition of glutamatergic neurotransmission by antagonizing N-methyl-D-aspartate (NMDA) receptors, it has been demonstrated that chronic alcohol exposure induced the upregulation of NMDA receptors that results from chronic inhibition of glutamate transmission as a compensatory mechanism (Gonzales, R. A. and J. N. Jaworski, *Alcohol and glutamate. Alcohol Health Res World,* 1997. 21(2): p. 120-7). In addition, chronic alcohol exposure also increases extracellular glutamate levels and enhances NMDA sensitivity in brain of alcohol dependence or withdrawal, suggesting glutamate-mediated excitotoxicity offers a plausible mechanism for some of the neuronal losses and cognitive deficits associated with chronic alcoholism. In addition, it can be reasonably speculated that glutamate-mediated excitotoxicity also plays a role in other substances-induced neuron loss and consequently psychosis due to the elevation of extracellular glutamate.

The cystine-glutamate antiporter or system $x_c^-$ is a membrane-bound $Na^+$-independent amino acid transporter that is structurally composed of a heavy chain subunit common to all amino acid transporters, 4F2hc, and a light chain specific subunit, xCT (Bridges, R. J., N. R. Natale, and S. A. Patel, *System xc(−) cystine/glutamate antiporter: an update on molecular pharmacology and roles within the CNS. Br J Pharmacol,* 2012. 165(1): p. 20-34 and Sato, H., et al., *Cloning and expression of a plasma membrane cystine/glutamate exchange transporter composed of two distinct proteins. J Biol Chem,* 1999. 274(17): p. 11455-8). The system $x_c^-$ exchanges intracellular glutamate for extracellular cystine, thereby supporting intracellular glutathione (GSH) synthesis as well as nonvesicular glutamate release. Therefore, most of studies focused on its role on oxidative stress in cancer or other diseases (Buckingham, S.C., et al., *Glutamate release by primary brain tumors induces epileptic activity. Nat Med,* 2011. 17(10): p. 1269-74 and Albrecht, P., et al., *Mechanisms of oxidative glutamate toxicity: the glutamate/cystine antiporter system xc− as a neuroprotective drug target. CNS Neurol Disord Drug Targets,* 2010. 9(3): p. 373-82). However, recent results derived from $x_c^-$ knockout mice indicate that loss of system $x_c^-$ does not induce oxidative stress but decreases extracellular glutamate in brain, suggesting system $x_c^-$ is an important source of extracellular glutamate involved in glutamatergic transmission and glutamate-mediated excitotoxicity (De Bundel, D., et al., *Loss of system x(c)− does not induce oxidative stress but decreases extracellular glutamate in hippocampus and influences spatial working memory and limbic seizure susceptibility. J Neurosci,* 2011. 31(15): p. 5792-803).

The dysregulation of system $x_c^-$ has been linked with addiction because the reduction in extracellular glutamate after chronic treatment with either cocaine or nicotine resulted from reduced system $x_c^-$ activity and levels of xCT expression in the accumbens (Baker, D. A., et al., *Neuroadaptations in cystine glutamate exchange underlie cocaine relapse. Nat Neurosci,* 2003. 6(7): p. 743-9; Knackstedt, L. A., et al., *The role of cystine-glutamate exchange in nicotine dependence in rats and humans. Biol Psychiatry,* 2009. 65(10): p. 841-5). Moreover, the restoration of system $x_c^-$ activity by its activator N-acetylcysteine (NAC) prevents reinstated cocaine or nicotine seeking behaviors. However, the period of system $x_c^-$ downregulation has not been directly determined in these mice. Recent studies demonstrated that the expression of system $x_c^-$ subunit xCT in brain was upregulated in alcohol dependence mice but downregulated in alcohol withdrawal rats (Peana, A. T, G. Muggironi, and F. Bennardini, *Change of cystine/glutamate antiporter expression in ethanol-dependent rats. Front Neurosci,* 2014. 8: p. 311), suggesting a dynamic change in xCT expression and its activity during addiction. Besides, system $x_c^-$ is not the only target for NAC and all pharmacological inhibitors commonly used to study system $x_c^-$ activity have off-target effects (Lewerenz, J., et al., *The cystine/glutamate antiporter system x(c)(−) in health and disease: from molecular mechanisms to novel therapeutic opportunities. Antioxid Redox Signal,* 2013. 18(5): p. 522-55). These issues raise the uncertain role of system $x_c^-$ in addiction.

SUMMARY OF THE INVENTION

The invention first found that the system $x_c^-$ knockout display an inhibition in alcohol and cocaine-mediated addiction and brain damage. Blockage of system $x_c^-$ by drugs improve substances seeking and craving behaviours and inhibit substances-induced brain damages. These findings show the inhibitors of system $x_c^-$ represent new class of therapeutics for treatment of substance-related and addictive disorders.

The invention provides a method for treating, preventing or reversing a substance-related and addictive disorder or a brain damage induced by substance-related and addictive disorder, comprising administering a therapeutically effective amount of a cystine-glutamate transporter inhibitor to a subject.

In some embodiments, the cystine-glutamate transporter inhibitor may be administered prior to or after the onset of physical or histological symptoms of substance-related and addictive disorder or brain damage induced by substance-related and addictive disorder. In some embodiments, the substance use disorder includes, but is not limited to, drug addiction, drug abuse, drug habituation, drug dependence, withdrawal syndrome and overdose. In some embodiments, the substance or addictive agent includes but is not limited to opiate, opioid, cocaine, morphine, amphetamines, nicotine, alcohol, heroin, ketamine, amphetamine, methamphetamine, cannabis, cannabinoid, benzodiazepine hallucinogen, ecstasy, barbiturate, marijuana, phencyclidine, narcotic analgesic combinations, narcotic analgesics, anxiolytics, sedatives, and hypnotics.

In one embodiment, the cystine-glutamate transporter inhibitor is system $x_c^-$ inhibitor. Preferably, the system $x_c^-$ inhibitor is sorafenib, regorafenib, sulfasalazine, erastin, L-glutamate, L-cystine, L-alpha-aminoadipate, L-alpha-aminopimelate, L-homocysteate, L-b-N-oxalyl-L-a,b-diaminopropionate (beta-L-ODAP), L-alanosine, ibotenate, L-serine-O-sulphate, (RS)-4-bromohomoibotenate, quisqualate, (S)-4-carboxyphenylglycine, RS-4-Br-Homo-IBO, 2-amino-3-(5-methyl-3-oxo-1,2-oxazol-4-yl)propanoic acid (AMPA), Arachidonylcyclopropylamide (ACPA), N-acetylamino-3-chloro-N-(2-diethylaminoethyl) benzamide (NACPA), TFMIH, NEIH, (S)-4-carboxyphenyglycine (4-S-CPG), 4-S-SPG, TSA or CPPG.

In one embodiment, the therapeutically effective amount for the substance-related and addictive disorder or brain damage induced by substance-related and addictive disorder ranges from about 50 mg/kg/dose to about 1000 mg/kg/dose.

In particular embodiments, the therapeutically effective amount of sulfasalazine ranges from 100 mg/kg/dose to about 1000 mg/kg/dose, that of sorafenib ranges from 50 mg/kg mg/kg/dose to about 400 mg/kg/dose and that of regorafenib ranges from 50 mg/kg mg/kg/dose to about 400 mg/kg/dose. The preferred ranges within the above-mentioned ranges of sulfasalazine, sorafenib and regorafenib are those described in previous paragraph.

In some embodiment, the cystine-glutamate transporter inhibitor may be administered with an additional therapeutic agent or an alternative therapy.

BRIEF DESCRIPTION OF THE DRAWING

FIGS. 1 A to D show alcohol consumption, preference, taste preference, water consumption in xCT knockout (KO) mice and wild-type (WT) mice. Alcohol consumption (A) and preference (B) of xCT KO mice in a two-bottle choice experiment. No differences in taste preference (C) for saccharin (sweet) and quinine (bitter) or in water consumption (D). Data are means±SD (n=6-8). *P<0.01 compared to WT mice.

FIGS. 2 A and B show that genetic deficiency and pharmacological inhibition of system $x_c^-$ decreases daily alcohol consumption. (A) The daily alcohol consumption in wild-type (WT) and xCT knockout (KO) mice with chronic alcohol exposure followed by free-choice drinking. xCT KO and WT mice were received chronic alcohol exposure via feeding the alcoholic liquid diet for 14 days and then presented in free-choice drinking model with 2 bottles, one containing diluted ethanol and the other containing water, providing a choice to the mice, for 7 days. (B) The daily alcohol consumption in WT with chronic alcohol exposure followed by vehicle, sulfasalazine (SAS, 15 mg/kg/day, i.p.), sorafenib (30 mg/kg i.p.) and regorafenib (30 mg/kg i.p.) treatment for 7 days during free-choice drinking. Data are means±SD (n=6-8). *P<0.0001 compared to water. #P<0.0001 compared to WT mice or vehicle treatment.

FIGS. 3 A to D show that genetic deficiency and pharmacological inhibition of system $x_c^-$ decreases daily cocaine consumption. (A and B) The daily cocaine consumption in wild-type (WT) and xCT knockout (KO) mice with chronic cocaine exposure followed by free-choice drinking. xCT KO and WT mice were received chronic cocaine exposure via intraperitoneal (i.p., 15 mg/kg) injection of cocaine for 7 days and then presented in free-choice drinking model with 2 bottles, one containing diluted cocaine and the other containing water, providing a choice to the mice, for 8 days. (C and D) The daily cocaine consumption in WT mice with chronic cocaine exposure followed by vehicle and sulfasalazine treatment (SAS, 15 mg/kg/day, i.p.) for 6 days during free-choice drinking. Data are means±SD (n=6-12). Data are means±SD *P<0.001 compared to water.

FIGS. 4 A and B show that genetic deficiency and pharmacological inhibition of system $x_c^-$ inhibit chronic alcohol exposure-induced apoptosis in brain. (A) The number of TUNEL-positive cells in frontal cortex derived from wild-type (WT) and xCT knockout (KO) mice with or without chronic alcohol exposure. xCT KO and WT mice were received chronic alcohol exposure via feeding the alcoholic liquid diet for 14 days. (B) The number of TUNEL-positive cells in frontal cortex derived from WT mice with chronic alcohol exposure followed by vehicle, sulfasalazine (SAS, 15 mg/kg/day, i.p.), sorafenib (30 mg/kg i.p.) and regorafenib (30 mg/kg i.p.) treatment for 14 days. Data are means±SD (n=6). *P<0.001 compared to control or vehicle group.

FIGS. 5 A and B show that genetic deficiency and pharmacological inhibition of system $x_c^-$ inhibit chronic cocaine exposure-induced apoptosis in brain. (A) The number of TUNEL-positive cells in frontal cortex derived from wild type (WT) and xCT knockout (KO) mice with or without chronic cocaine exposure. xCT KO and wild type mice were received chronic cocaine exposure via intraperitoneal (i.p., 15 mg/kg) injection of cocaine for 7 days. (B) The number of TUNEL-positive cells in frontal cortex derived from WT mice with chronic cocainee exposure followed by vehicle or sulfasalazine (SAS, 15 mg/kg/day, i.p.) treatment for 7 days. Data are means±SD (n=6). *P<0.001 compared to control or vehicle group.

DETAILED DESCRIPTION OF THE INVENTION

The prior art discloses a decrease in system $x_c^-$ activity in cocaine-withdrawn rats, thus suggesting activation of system $x_c^-$ activity to reinstate cocaine or nicotine seeking behaviors. Contrary to the prior art, the invention surprisingly found that agents that inhibit system $x_c^-$ provide the therapeutic intervention in substance-related and addictive disorders and the treatment and/or prevention in brain damage and confirms that system $x_c^-$ is a promising therapeutic target for substance-related addiction and brain damage induced by substance-related and addictive disorder.

As used in this specification and the appended claims, the singular forms "a," "an" and "the" include plural references unless the content clearly dictates otherwise.

As used herein, the term "prevent," and similar word such as "prevention," "preventing", is an approach for preventing the onset or recurrence of a disease or condition, or preventing the occurrence or recurrence of the symptoms of a disease or condition, or optionally an approach for delaying the onset or recurrence of a disease or condition or delaying the occurrence or recurrence of the symptoms of a disease or condition.

As used herein, the terms "treating" or "treatment of" a disease state includes: 1) inhibiting the disease state, i.e., arresting the development of the disease state or its clinical symptoms; 2) or relieving the disease state, i.e., causing temporary or permanent regression of the disease state or its clinical symptoms.

As used herein, the terms "co-administration" or the like, as used herein, are meant to encompass administration of the selected therapeutic agents to a single patient, and are intended to include treatment regimens in which the agents are administered by the same or different route of administration or at the same or different time.

As used herein, the term "therapeutically effective amount" refers to that amount of an inhibitor described herein that is sufficient to effect treatment, as defined below, when administered to a patient in need of such treatment. The therapeutically effective amount will vary depending upon the specific activity of the therapeutic agent being used, and the age, physical condition, existence of other disease states, and nutritional status of the patient.

As used herein, the term "brain damage induced by substance-related and addictive disorder" results in mental and behavioral disorders due to psychoactive substance use (see F10-F19, Mental and behavioral disorders due to psychoactive substance use, The ICD-10 Classification of Mental and Behavioural Disorders: Clinical descriptions and diagnostic guidelines, World Health Organization). The disorders include but are not limited to mental disorder, schizophrenia-like, predominantly delusional, hallucinatory, depressive, manic, psychotic phenomena, amnesic syndrome, sudden change of consciousness with aggressive behavior and amnesia, dementia, hallucinosis, wernicke encephalopathy and Korsakov's psychosis.

As used herein, the term "addiction" broadly encompasses the process whereby physical and/or psychological dependence develops to a drug. The withdrawal symptoms can reinforce the addiction, driving the user to continue taking the drug.

As used herein, the term "substance use disorder" also known as drug use disorder, is a condition in which the use of one or more substances leads to a clinically significant impairment or distress. The term "drug addiction" refers to a state of periodic or chronic intoxication produced by the repeated consumption of a drug (natural or synthetic).

As used herein, the term "physical dependence" (or "drug dependence") refers to a state resulting from habitual use of a drug, where negative physical withdrawal symptoms result from abrupt discontinuation.

As used herein, the term "addictive agent(s)" includes any and all agents to which a subject can become addicted, either physically or psychologically, or both. As noted above, addiction includes addiction to chemical entities, such as drugs, as well as addiction to behaviors, as in impulse control disorders.

As used herein, the term "mammalian subject" includes all mammals, including without limitation humans, non-human primates, dogs, cats, horses, sheep, goats, cows, rabbits, pigs, and rodents.

As used herein, the term "system $x_c^-$" refers to an amino acid antiporter that typically mediates the exchange of extracellular L-cystine and intracellular L-glutamate across the cellular plasma membrane.

In one aspect, the invention provides a method for treating, preventing or reversing a substance-related and addictive disorder or a brain damage induced by substance-related and addictive disorder, comprising administering a therapeutically effective amount of a cystine-glutamate transporter inhibitor to a subject. Accordingly, the invention provides a use of a cystine-glutamate transporter inhibitor in the manufacture of a medicament for treating, preventing or reversing substance-related and addictive disorder or a brain damage induced by substance-related and addictive disorder. Alternatively, the invention provides a cystine-glutamate transporter for treating, preventing or reversing a substance-related and addictive disorder or a brain damage induced by substance-related and addictive disorder.

The cystine-glutamate transporter inhibitor may be administered prior to or after the onset of physical or histological symptoms of substance-related and addictive disorder or a brain damage induced by substance-related and addictive disorder.

In some embodiments, the substance-related disorder includes, but is not limited to, drug addiction, drug abuse, drug habituation, drug dependence, withdrawal syndrome and overdose. In a further embodiment, the substance-related disorder is a drug addiction. In some embodiments, the substance or addictive agent includes but is not limited to opiate, opioid, cocaine, morphine, amphetamines, nicotine, alcohol, heroin, ketamine, amphetamine, methamphetamine, cannabis, cannabinoid, benzodiazepine hallucinogen, ecstasy, barbiturate, marijuana, phencyclidine, narcotic analgesic combinations, narcotic analgesics, anxiolytics, sedatives, and hypnotics.

In a further embodiment, the substance-related disorder is alcohol consumption, alcohol dependence or alcohol abuse.

In one embodiment, the brain damage induced by substance-related and addictive disorder results in mental and behavioral disorders due to psychoactive substance use. In some embodiments, the disorders include but are not limited to mental disorder, schizophrenia-like, predominantly delusional, hallucinatory, depressive, manic, psychotic phenomena, amnesic syndrome, sudden change of consciousness with aggressive behavior and amnesia, dementia, hallucinosis, wernicke encephalopathy and Korsakov's psychosis.

In one embodiment, the cystine-glutamate transporter inhibitor is system $x_c^-$ inhibitor.

In one embodiment, the system $x_c^-$ inhibitor is sorafenib, regorafenib, sulfasalazine, erastin, L-glutamate, L-cystine, L-alpha-aminoadipate, L-alpha-aminopimelate, L-homocysteate, L-b-N-oxalyl-L-a,b-diaminopropionate (beta-L-ODAP), L-alanosine, ibotenate, L-serine-O-sulphate, (RS)-4-bromohomoibotenate, quisqualate, (S)-4-carboxyphenylglycine, RS-4-Br-Homo-IBO, 2-amino-3-(5-methyl-3-oxo-1,2-oxazol-4-yl)propanoic acid (AMPA), Arachidonylcyclopropylamide (ACPA), N-acetylamino-3-chloro-N-(2-diethylaminoethyl)benzamide (NACPA), TFMIH, NEIH, (S)-4-carboxyphenylglycine (4-S-CPG), 4-S-SPG, TSA or CPPG.

In one embodiment, the therapeutically effective amount for a substance-related and addictive disorder or a brain damage induced by substance-related and addictive disorder ranges from 50 mg/kg/dose to about 1000 mg/kg/dose, 50 mg/kg/dose to about 900 mg/kg/dose, 50 mg/kg/dose to about 800 mg/kg/dose, 50 mg/kg/dose to about 700 mg/kg/dose, 50 mg/kg/dose to about 600 mg/kg/dose, 50 mg/kg/dose to about 500 mg/kg/dose, 50 mg/kg/dose to about 400 mg/kg/dose, 50 mg/kg/dose to about 300 mg/kg/dose, 50 mg/kg/dose to about 200 mg/kg/dose, 50 mg/kg/dose to about 100 mg/kg/dose, 100 mg/kg/dose to about 1000 mg/kg/dose, 100 mg/kg/dose to about 900 mg/kg/dose, 100 mg/kg/dose to about 800 mg/kg/dose, 100 mg/kg/dose to about 700 mg/kg/dose, 100 mg/kg/dose to about 600 mg/kg/dose, 100 mg/kg/dose to about 500 mg/kg/dose, 100 mg/kg/dose to about 400 mg/kg/dose, 100 mg/kg/dose to about 300 mg/kg/dose, 100 mg/kg/dose to about 200 mg/kg/dose, 200 mg/kg/dose to about 1000 mg/kg/dose, 200 mg/kg/dose to about 900 mg/kg/dose, 200 mg/kg/dose to about 800 mg/kg/dose, 200 mg/kg/dose to about 700 mg/kg/dose, 200 mg/kg/dose to about 600 mg/kg/dose, 200 mg/kg/dose to about 500 mg/kg/dose, 200 mg/kg/dose to about 400 mg/kg/dose, 200 mg/kg/dose to about 300 mg/kg/dose, 300 mg/kg/dose to about 1000 mg/kg/dose, 300 mg/kg/dose to about 900 mg/kg/dose, 300 mg/kg/dose to about 800 mg/kg/dose, 300 mg/kg/dose to about 700 mg/kg/dose, 300 mg/kg/dose to about 600 mg/kg/dose, 300 mg/kg/dose to about 500 mg/kg/dose, 300 mg/kg/dose to about 400 mg/kg/dose, 400 mg/kg/dose to about 1000 mg/kg/dose, 400 mg/kg/dose to about 900 mg/kg/dose, 400 mg/kg/dose to about 800 mg/kg/dose, 400 mg/kg/dose to about 700 mg/kg/dose, 400 mg/kg/dose to about 600 mg/kg/dose, 400 mg/kg/dose to about 500 mg/kg/dose, 500 mg/kg/dose to about 1000 mg/kg/dose, 500 mg/kg/dose to about 900 mg/kg/dose, 500 mg/kg/dose to about 800 mg/kg/dose, 500 mg/kg/dose to about 700 mg/kg/dose, 500 mg/kg/dose to about 600 mg/kg/dose, 600 mg/kg/dose to about 1000 mg/kg/dose, 700 mg/kg/dose to about 1000 mg/kg/dose, 800 mg/kg/dose to about 1000 mg/kg/dose or 900 mg/kg/dose to about 1000 mg/kg/dose.

In some embodiment, the cystine-glutamate transporter inhibitor may be administered with an additional therapeutic agent or an alternative therapy. The administration means alone or "in combination with" one or more further therapeutic agents includes simultaneous (concurrent) and consecutive administration in any order. In some embodiment, the additional therapeutic agent is morphine, methadone, noribogaine, ibogaine, narcotic analgesic combinations, narcotic analgesics, anxiolytics, sedatives, and hypnotics.

The cystine-glutamate transporter inhibitor may be formulation as composition in various forms. For example, it can be a soft chew composition, powder, emulsion composition, aqueous composition, capsule, tablet or gel.

Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection. In certain embodiments, the pharmaceutical compositions of the invention are formulated for intravenous or subcutaneous administration. Such compositions would normally be administered as pharmaceutically acceptable compositions as described herein.

The cystine-glutamate transporter inhibitors may also be administered parenterally or intraperitoneally. By way of illustration, solutions of cystine-glutamate transporter inhibitors as free base or pharmacologically acceptable salts can be prepared in water suitably mixed with a surfactant. Dispersions can also be prepared in glycerol, liquid polyethylene glycols, and mixtures thereof and in oils. Under ordinary conditions of storage and use, these preparations generally contain a preservative to prevent the growth of microorganisms.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more excipients or carriers. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating.

Formulations suitable for topical administration in the mouth include lozenges comprising the active ingredient in a flavored basis, usually sucrose and acacia or tragacanth;

pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods.

EXAMPLES

Material and Methods
Animals

All animals were treated according to the Institutional Guidelines of China Medical University and approved by the Institutional Animal Care and Use Committees of China Medical University. C57BL/6J mice used for wild-type were purchased from the Animal Facility of the National Science Counsel (NSC). xCT homozygous knockout (xCT$^{-/-}$) mice of 129/Svj-C57BL/6J mixed genetic background and their genotyping were as described previously [25]. xCT$^{-/-}$ mice kindly provided by Dr. Hideyo Sato.
Free-Choice Two-Bottle Drinking Behavior Test Mice were habituated to drinking water from two bottles for 1 week and then, mice were given 24 h access to two bottles, one containing water and the other containing an alcohol solution. The concentration of alcohol was increased every fourteenth day. The consumption of alcohol and water and animal weight was recorded four times for each alcohol concentration with 2 day intervals. For the potential differences in taste preference, two weeks after the alcohol self-administration procedure, the same mice were tested for saccharin (sweet) and quinine (bitter) fluid intake and preference by administering 0.055% saccharin solutions both for 1 week. After a recovery for 1 week with two bottles of water, the mice were treated 20 µM quinine solutions both for 1 week. The saccharin and quinine solutions consumptions were determined for each concentration twice with 2-day intervals. During the alcohol self-administration experiment, average alcohol consumption per day per body weight was calculated for each measurement. The density of alcohol (0.79 g/l) was taken into account in the calculations. For the chronic alcohol exposure, mice were given the liquid diet without ethanol for 7 days at the beginning of the study. Then, liquid diet, for inducing alcohol dependence, was gradually enriched with 2.4% (3 days), 4.8% (4 days) and 7.2% (14 days) alcohol. After chronic alcohol exposure, mice were presented in free-choice drinking model with 2 bottles, one containing diluted ethanol (7.2%) and the other containing water, providing a choice to the mice, for 7 days. For the chronic cocaine exposure, mice were intraperitoneally injected with 15 mg/kg cocaine for 7 days to generate cocaine-dependent mice before free choice experiments. Water and 0.15 mg/ml cocaine were given in two-bottle free-choice paradigm for 6 days. Intakes were recorded every day.
Primary Cortical Cells Preparation Primary cortical cells were prepared from cerebral cortices of wild-type C57BL/6J or xCT homozygous knockout (xCT KO) mouse embryos in embryonic day 17 as previously described in Shyu, W. C., et al., *Secretoneurin pro-motes neuroprotection and neuronal plasticity via the Jak2/Stat3 pathway in murine models of stroke. J Clin Invest*, 2008. 118(1): p. 133-48.
TUNEL Staining TUNEL staining in brain tissues was carried out by TUNEL Apoptosis Detection Kit (Millipore) according to the manufacturer's protocol. In brief, 10-µm frozen sections were incubated with proteinase K for 15 min at room temperature. Sections were incubated with terminal deoxynucleotidyl transferase end-labeling cocktail for 60 min at 37° C. After washing and blocking, avidin-fluorescein isothiocyanate (1:10) was applied to the sections and incubated in the dark for 30 min at 37° C. Staining of nuclei was expressed as the percentage of TUNEL-positive apoptotic cells among 1000 cells in each brain. TUNEL-positive cells were counted in 40 high-power fields in 10 different sections of each of two brains, 100 cells/section.
Apoptosis Assay Annexin V staining was performed to determine cell apoptosis using the Annexin V-FITC Apoptosis Detection Kit (Sigma-Aldrich) for 10 minutes at room temperature according to the manufacturer's instructions, and then flow cytometric analysis was performed.
Statistical Analysis All data are given as mean±SD. Statistical analyses were performed with SPSS 18.0 software using unpaired Student's t test and ANOVA with Bonferroni's or Tukey's multiple comparison post hoc tests, where appropriate.

Example 1 Role of System $x_c^-$ on Addiction

Figure 1A:
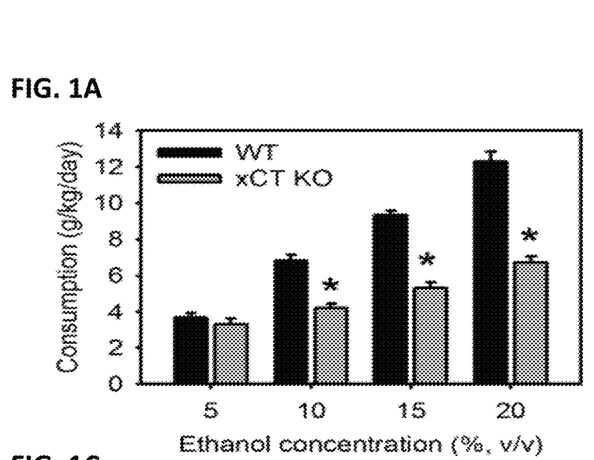
Figure 1B:
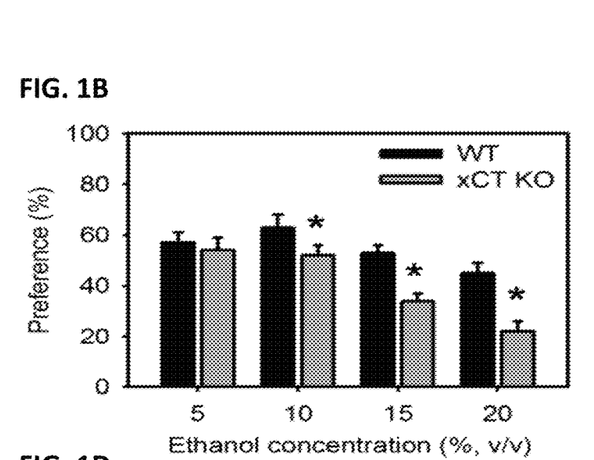
Figure 1C:
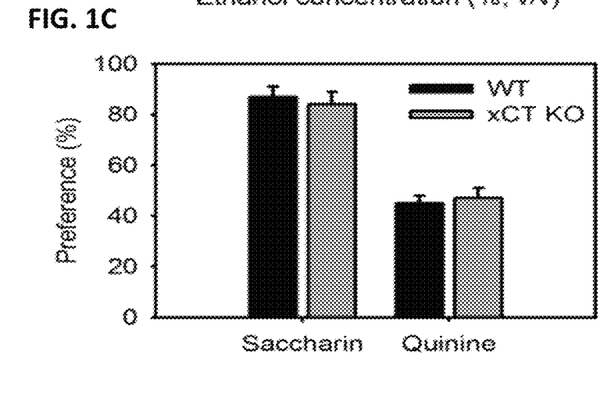
Figure 1D:
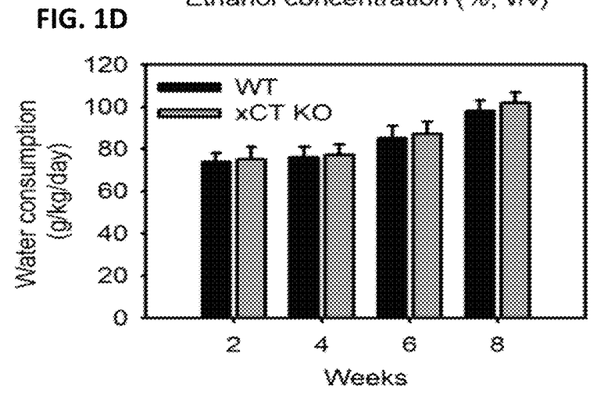
Figure 2A:
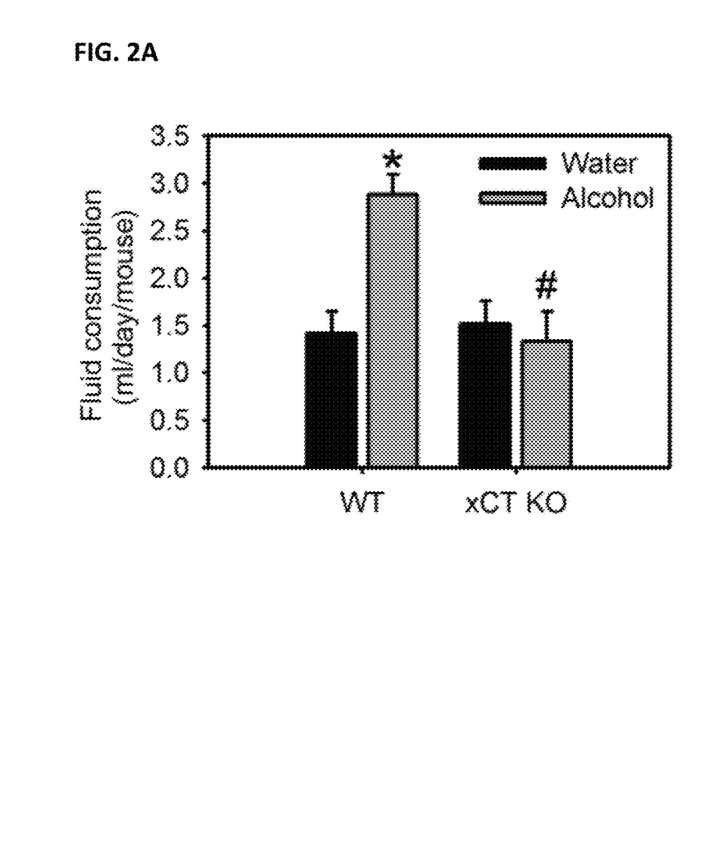

In an attempt to gain insight into the role of system $x_c^-$ on addiction, we first utilized the free-choice two-bottle drinking behavior test to determine alcohol self-administration and preference. xCT knockout (KO) mice consumed significantly less alcohol than wild-type (WT) mice (FIG. 1A). Moreover, there was significant decrease in alcohol preference in xCT KO mice as compared to WT mice (FIG. 1B). There were no significant differences in saccharin or quinine preference between xCT KO mice and WT mice (FIG. 1C) indicating that alcohol avoidance of xCT KO mice is not due to taste neophobia. Water consumption of the two genotypes was not significantly different throughout the experiment (FIG. 1D). In order to induce the alcohol dependence mice, xCT KO mice and WT mice were received chronic alcohol exposure via feeding the alcoholic liquid diet for 14 days and then presented in free-choice drinking model with 2 bottles during the ethanol access period, one containing diluted ethanol and the other containing water, providing a choice to the mice, for 7 days. The WT mice displayed an alcohol preference behavior after chronic alcohol exposure. However, this behavior didn't show in xCT KO mice. Moreover, there was significant decrease in daily alcohol consumption in xCT KO mice during free-choice drinking as compared to WT mice (FIG. 2A). These findings show that genetic deficiency of system $x_c^-$ decreased alcohol addiction.

Figure 2B:
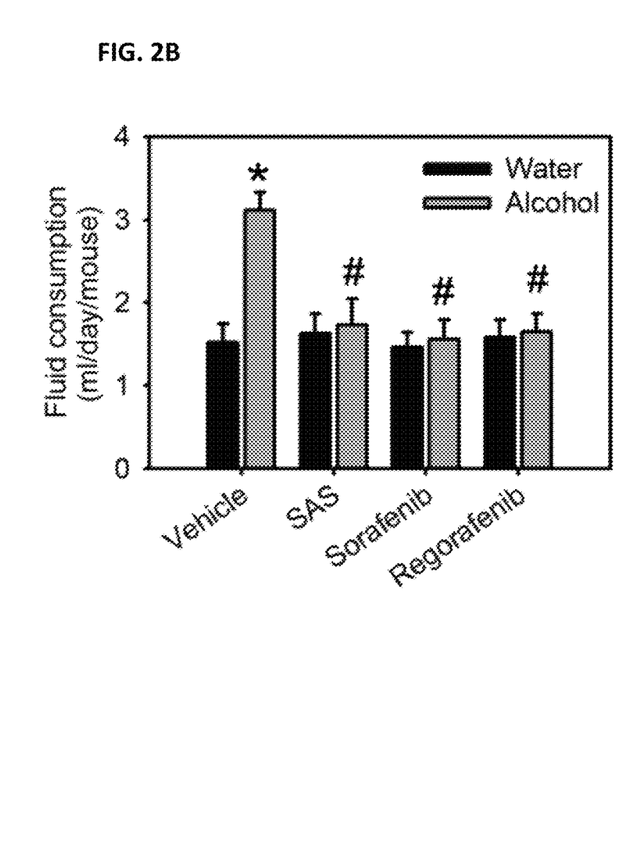

Example 2 Therapeutic Potential of Manipulation of System $x_c^-$ in Alcohol-Dependence We explored the therapeutic potential of manipulation of system $x_c^-$ in alcohol-dependence, sulfasalazine, sorafenib and regorafenib that blocks system $x_c^-$ (Buckingham, S.C., et al., *Glutamate release by primary brain tumors induces epileptic activity. Nat Med*, 2011. 17(10): p. 1269-74; Chung, W. J., et al., *Inhibition of cystine uptake disrupts the growth of primary brain tumors. J Neurosci*, 2005. 25(31):

p. 7101-10), were used to treat alcohol-dependent mice. Sulfasalazine, sorafenib and regorafenib significantly attenuated the daily alcohol consumption during free-choice drinking as compared to control vehicle (DMSO) (FIG. 2B). These results suggest that pharmacological inhibition of system $x_c^-$ via its inhibitors (i.e. sorafenib, regorafenib and sulfasalazine) improves alcohol addiction treatment.

Figure 3A:
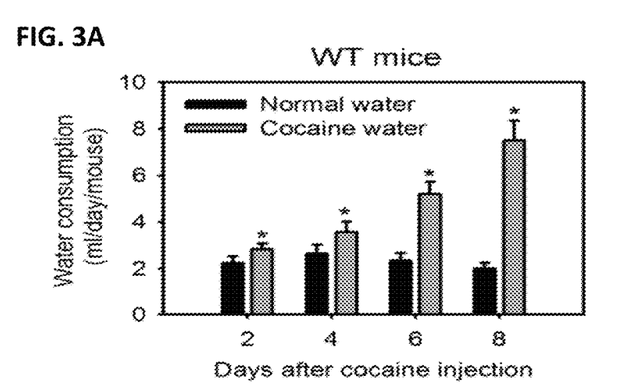
Figure 3B:
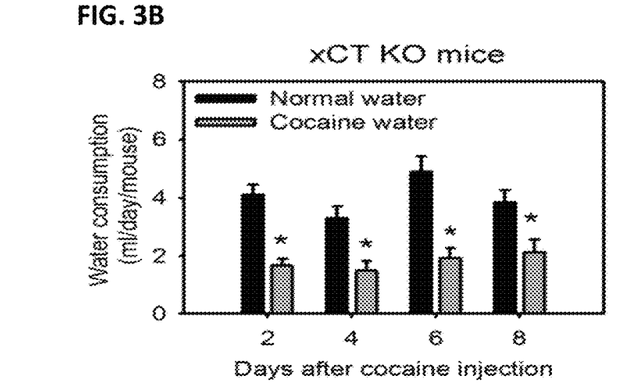
Figure 3C:
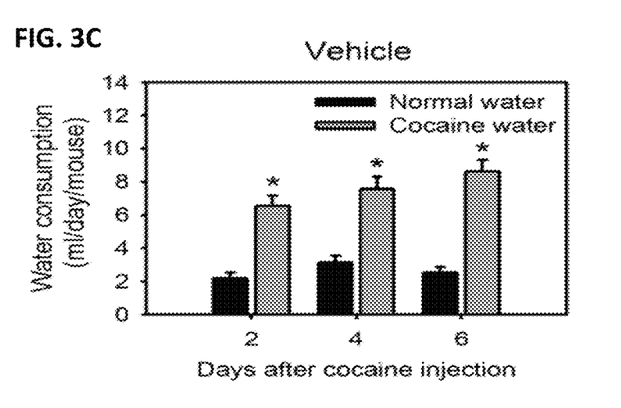
Figure 3D:
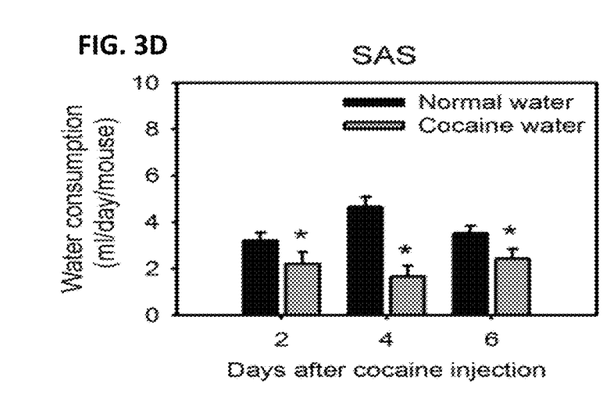

Example 3 Assay for Improvement of Cocaine Addiction Treatment and Alcohol Addiction Treatment To test whether system $x_c^-$ plays the same role in other substance-use disorders, xCT KO mice and WT mice were enforced to receive the intraperitoneal injection of cocaine for 7 days and then transferred to free-choice drinking model with 2 bottles, one containing diluted cocaine and the other containing normal water for 8 days. As well as alcohol-dependent mice, WT mice have cocaine preference behavior after chronic cocaine exposure and displayed a craving behavior (FIG. 3A). However, xCT KO mice were attempted to drink normal water, suggesting genetic deficiency of system $x_c^-$ suppressed cocaine addiction. In addition, cocaine-dependent WT mice were daily treated with sulfasalazine or vehicle after chronic cocaine exposure. Amazingly, sulfasalazine treatment fully inhibited cocaine preference and craving behaviours compared to vehicle treatment (FIG. 3B). These results show that blockage of system $x_c^-$ is able to improve cocaine addiction treatment as well as alcohol addiction treatment.

Figure 4A:
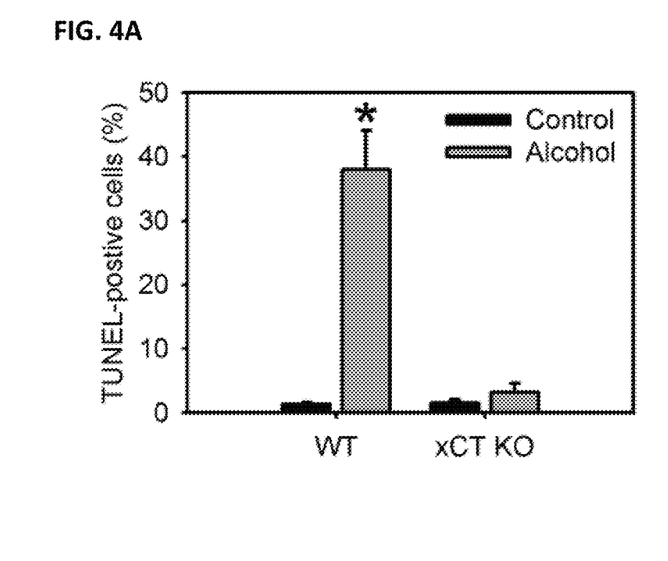
Figure 4B:
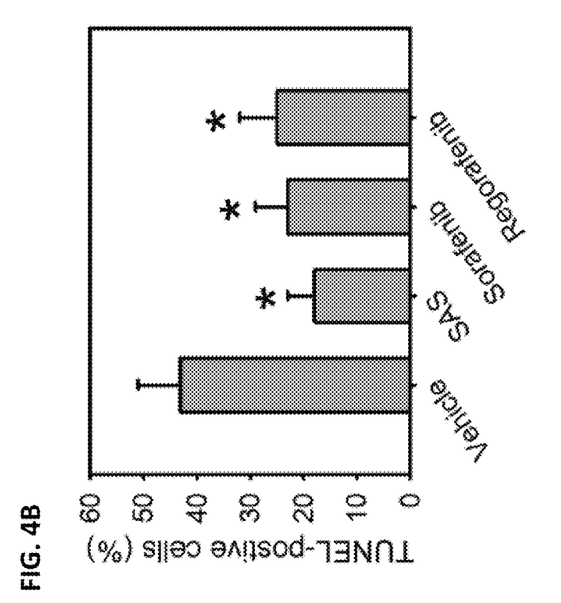

Example 4 Impact of System $x_c^-$ on Chronic Alcohol Exposure-Induced Apoptosis We determined the impact of system $x_c^-$ on chronic alcohol exposure-induced apoptosis. TUNEL immunofluorescence staining was utilized to observe the number of apoptotic cells in brain tissues derived from mice with or without chronic alcohol exposure. There was significant increase in TUNEL-positive cells in brain tissues from wild-type mice with chronic alcohol exposure compared to brain tissues from wild-type mice without chronic alcohol exposure (FIG. 4A), suggesting chronic alcohol exposure could trigger apoptosis in brain. Interestingly, xCT KO mice with or without chronic alcohol exposure had no significant difference in apoptotic cells (FIG. 4A), indicating system $x_c^-$ plays an important role in chronic alcohol exposure-induced apoptosis. Moreover, the treatments of sulfasalazine, sorafenib and regorafenib in wild-type mice during chronic alcohol exposure also inhibited apoptosis compared to vehicle treatment (FIG. 4B).

Example 5 Chronic Cocaine Treatment

Figure 5A:
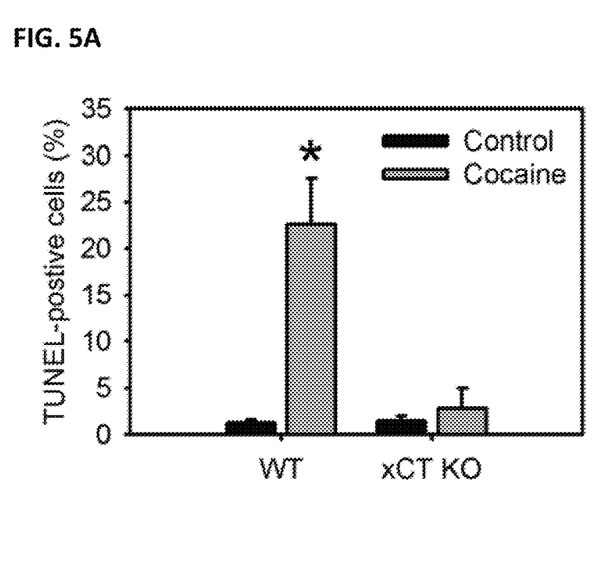
Figure 5B:
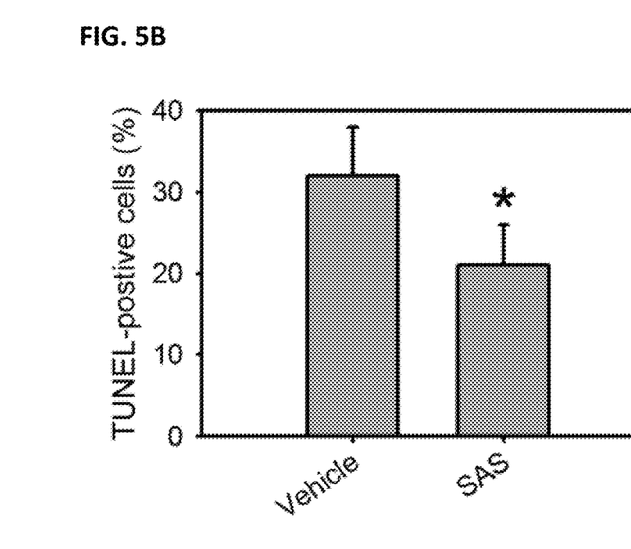
Figure 6:
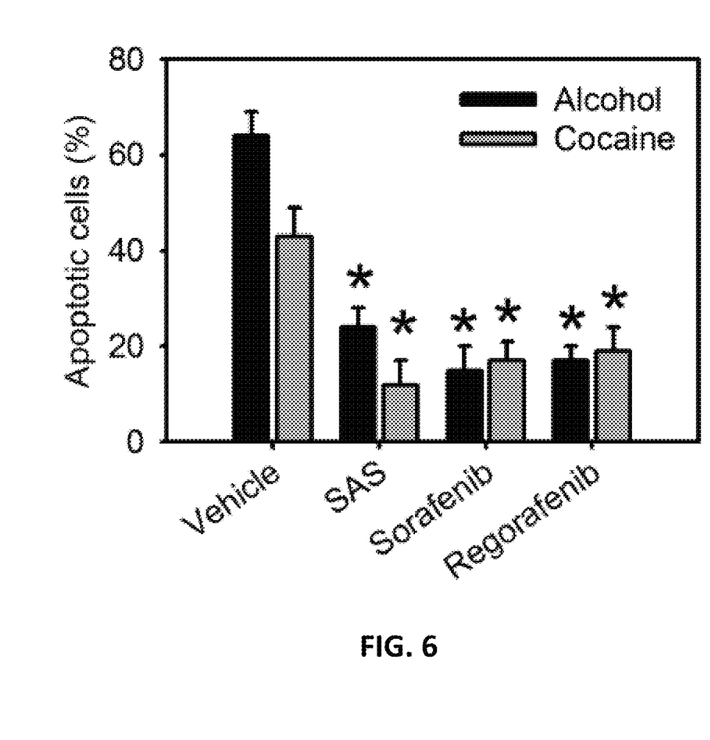
FIG. 6 shows that pharmacological inhibition of system $x_c^-$ protects primary cortical cells during alcohol or cocaine treatment. Apoptosis in wild-type cortical cells exposed to alcohol or cocaine with or without vehicle (DMSO), sulfasalazine (SAS, 500 µM), sorafenib (10 µM) and regorafenib (10 µM) or for 18 hours. # P<0.0001 compared to vehicle. Data are means±SD (n=3). *P<0.001 compared to vehicle group.

The similar effects were also able to observe in chronic cocaine treatment. The number of apoptotic cells were significantly increased in chronic cocaine-treated WT mice compared with control mice (FIG. 5A). However, no significant difference between groups was observed in xCT KO mice. Moreover, WT mice treated with sulfasalazine during chronic cocaine exposure exhibited significantly reduced the number of apoptotic cells compared with control mice (FIG. 5B). On the other hand, wild type cortical cells were treated with sulfasalazine, sorafenib or regorafenib for 18 hours during the alcohol or cocaine incubation. sulfasalazine, sorafenib and regorafenib significantly inhibited substance-induced apoptosis (FIG. 6). These results suggest that pharmacological inhibition of system $x_c^-$ with administration of system $x_c^-$ inhibitors significantly improves substance-induced brain damage treatment.

I claim:

1. A method for treating, preventing or reversing a substance-related and addictive disorders or a brain damage induced by substance-related and addictive disorder in a subject in need thereof, comprising administering a therapeutically effective amount of a cystine-glutamate transporter inhibitor to the subject, wherein the cysteine-glutamate transporter inhibitor is a system $x_c^-$ inhibitor selected from sorafenib, regorafenib, sulfasalazine, erastin, L-glutamate, L-cystine, L-alpha-aminoadipate, L-alpha-aminopimelate, L-homocysteate, L-b-N-oxalyl-L-a,b-diaminopropionate (beta-L-ODAP), L-alanosine, ibotenate, L-serine-O-sulphate, (RS)-4-bromohomoibotenate, quisqualate, (S)-4-carboxyphenylglycine, RS -4-Br-Homo-IBO, 2-amino-3-(5-methyl-3-oxo- 1,2-oxazol-4-yl)propanoic acid (AMPA), Arachidonylcyclopropylamide (ACPA), N-acetylamino-3-chloro-N-(2-diethylaminoethyl) benzamide (NACPA), TFMIH, NEIH, (S)-4-carboxyphenyglycine (4-S-CPG), 4-S-SPG, TSA or CPPG.

2. The method of claim 1, wherein the cystine-glutamate transporter inhibitor may be administered prior to or after the onset of physical or histological symptoms of the substance-related and addictive disorders or brain damage induced by substance-related and addictive disorder.

3. The method of claim 1, wherein the substance-related and addictive disorder is drug addiction, drug abuse, drug habituation, drug dependence, withdrawal syndrome or overdose.

4. The method of claim 3, wherein the substance-related and addictive disorder is a drug addiction.

5. The method of claim 3, wherein the substance-related and addictive disorder is alcohol consumption, alcohol dependence or alcohol abuse.

6. The method of claim 1, wherein the brain damage induced by substance-related and addictive disorder results in mental and behavioral disorders due to psychoactive substance use.

7. The method of claim 6, wherein the mental and behavioral disorders due to psychoactive substance use is mental disorder, schizophrenia-like, predominantly delusional, hallucinatory, depressive, manic, psychotic phenomena, amnesic syndrome, sudden change of consciousness with aggressive behavior and amnesia, dementia, hallucinosis, wernicke encephalopathy or Korsakov's psychosis.

8. The method of claim 1, wherein the substance or addictive agent is opiate, opioid, cocaine, morphine, amphetamines, nicotine, alcohol, heroin, ketamine, amphetamine, methamphetamine, cannabis, cannabinoid, benzodiazepine hallucinogen, ecstasy, barbiturate, marijuana, phencyclidine, narcotic analgesic combinations, narcotic analgesics, anxiolytics, sedatives, or hypnotics.

9. The method of claim 1, wherein the system $x_c^-$ inhibitor is sorafenib, regorafenib or sulfasalazine.

10. The method of claim 1, wherein the therapeutically effective amount ranges from about 50 mg/kg/dose to about 1000 mg/kg/dose.

11. The method of claim 9, wherein the therapeutically effective amount of sulfasalazine ranges from about 50 mg/kg/dose to about 1000 mg/kg/dose, that of sorafenib ranges from 50 mg/kg mg/kg/dose to about 400 mg/kg/dose and that of sorafenib ranges from 50 mg/kg mg/kg/dose to about 400 mg/kg/dose.

12. The method of claim 1, wherein the cystine-glutamate transporter inhibitor may be administered with an additional therapeutic agent or an alternative therapy.

13. The method of claim 12, wherein the cystine-glutamate transporter inhibitor and the additional therapeutic agent are administered simultaneously, separately or consecutively.

14. The method of claim 12, wherein the additional therapeutic agent is morphine, methadone, noribogaine, ibogaine, narcotic analgesic combinations, narcotic analgesics, anxiolytics, sedatives, and hypnotics.

15. The method of claim 1, which can be formulated as soft chew composition, powder, emulsion composition, aqueous composition, capsule, tablet, gel or long-acting injectable liquid.

16. The method of claim 1, which can be administered orally, parenterally, subcutaneously, intramuscularly, intraperitoneally, intravenously, topically, intrapulmonary or nasally.

* * * * *